United States Patent
Riera Giner et al.

(10) Patent No.: US 9,504,765 B2
(45) Date of Patent: Nov. 29, 2016

(54) ACTIVE SUBSTANCE DISPENSING DEVICE

(71) Applicant: ZOBELE ESPANA, S.A., Barcelona (ES)

(72) Inventors: Montserrat Riera Giner, Barcelona (ES); Julio Cesar Ruiz Ballesteros, Barcelona (ES); Cedric Gobber, Barcelona (ES)

(73) Assignee: ZOBELE ESPANA, S.A., Barcelona (ES)

( * ) Notice: Subject to any disclaimer, the term of this patent is extended or adjusted under 35 U.S.C. 154(b) by 0 days.

(21) Appl. No.: 14/767,481

(22) PCT Filed: Jan. 10, 2014

(86) PCT No.: PCT/ES2014/070012
§ 371 (c)(1),
(2) Date: Aug. 12, 2015

(87) PCT Pub. No.: WO2014/125140
PCT Pub. Date: Aug. 21, 2014

(65) Prior Publication Data
US 2015/0374872 A1 Dec. 31, 2015

(30) Foreign Application Priority Data
Feb. 18, 2013 (EP) .................................. 13382047

(51) Int. Cl.
*A24F 25/00* (2006.01)
*A61L 9/04* (2006.01)
(Continued)

(52) U.S. Cl.
CPC ............... *A61L 9/12* (2013.01); *D06F 39/024* (2013.01)

(58) Field of Classification Search
CPC ......... A61L 9/12; A61L 9/127; A61L 9/125; B60H 3/0007; B60H 2003/0064; D06F 39/024
USPC ................................ 239/44, 47, 49, 51.5, 55
See application file for complete search history.

(56) References Cited

U.S. PATENT DOCUMENTS

| 4,014,501 A | 3/1977 | Buckenmayer |
| 4,372,490 A | 2/1983 | Le Caire, Jr. et al. |

(Continued)

FOREIGN PATENT DOCUMENTS

| ES | 1052937 | 3/2003 |
| FR | 2813563 | 3/2002 |
| WO | 91/04368 | 4/1991 |

OTHER PUBLICATIONS

Supplementary European Search Report for EP14751876.5, Mailed Sep. 20, 2016.

*Primary Examiner* — Davis Hwu
(74) *Attorney, Agent, or Firm* — Kutak Rock LLP; Bryan P. Stanley

(57) ABSTRACT

The dispensing device comprising an active substance dispensing element (1) and adjustment means of the dispensing of said active substances, said active substance dispensing element (1) being housed inside a casing (2) formed by a first body (3) and a second body (4) that can be coupled to each other and that can rotate with respect to each other, said adjustment means comprising an opening (5) provided in said first body (3) and at least one tab (6), such that the relative position between said first (3) and second (4) bodies determines the degree of closure of said opening (5) by means of said tab (6), and in that said first body (3) comprises holes (7) supplementary to a protrusion (8), the position of said protrusion (8) inside one of said holes (7) determining varying adjustment positions of the degree of closure of said opening.

5 Claims, 2 Drawing Sheets

(51) Int. Cl.
*A61L 9/12* (2006.01)
*D06F 39/02* (2006.01)

(56) References Cited

U.S. PATENT DOCUMENTS

| | | | |
|---|---|---|---|
| 4,878,615 A * | 11/1989 | Losi | A61L 9/12 239/45 |
| 5,988,520 A | 11/1999 | Bitner | |
| 6,569,387 B1 * | 5/2003 | Furner | A01M 1/2033 222/183 |
| 7,244,398 B2 * | 7/2007 | Kotary | A61L 9/042 239/34 |
| 7,303,143 B2 * | 12/2007 | Davis | A61L 9/037 239/145 |
| 8,048,379 B2 * | 11/2011 | Sassoon | A01M 1/2033 206/485 |
| D664,246 S | 7/2012 | Irvin et al. | |
| 2007/0207067 A1 | 9/2007 | Zarembinski | |
| 2011/0052450 A1 | 3/2011 | Chao | |

* cited by examiner

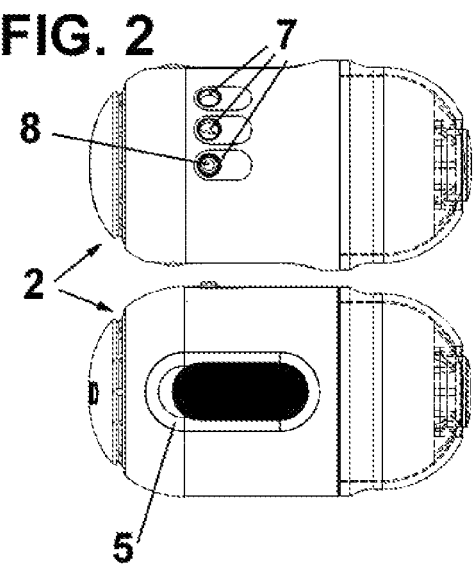
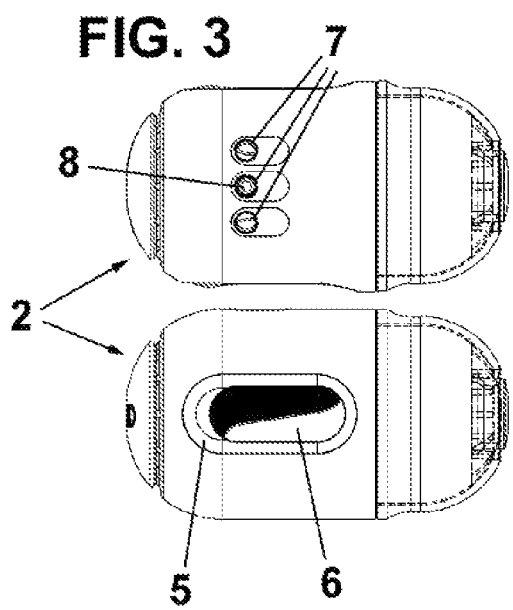
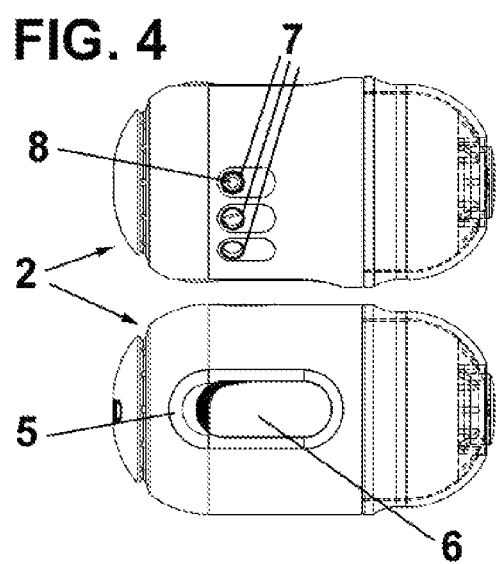

ACTIVE SUBSTANCE DISPENSING DEVICE

This is the United States National Stage of Patent Cooperation Treaty Application No. PCT/ES2014/070012 filed Jan. 10, 2014, which claims priority to European Patent Application No. 13382047.2 filed Feb. 18, 2013, the disclosures of which are incorporated herein by reference in their entireties.

This invention relates to an active substance dispensing device intended to treat the medium surrounding the device, including air, such as air fresheners or insecticides, or water, such as soap products, bleaches, or cleaning products, making it possible to adjust the active substances being dispensed.

BACKGROUND OF THE INVENTION

There are devices in the market that make it possible to dispense active substances to treat air or water, such as air fresheners or insecticides, that are also subject to adjustment.

This adjustment is generally achieved by opening or closing a window in varying degrees to adjust the level of communication between an internal chamber where the active substance is and the external fluid medium (air or water).

In currently known dispensing devices, adjustment is achieved with the friction of the different parts of the device or the addition of a small interference among the parts, such that changes in the adjustment produce a click that is audible to the user.

These dispensing devices are designed for use in static locations because they are not prepared for use in places where they could be subjected to random or abrupt movements, such as, for example, in washing machines, sports bags, etc., where the device may be subjected to external friction that could cause an alteration of the adjustment level selected by the user.

Therefore, the need for a dispensing device that makes it possible to adjust the dispensing of active substances and that can be used in certain places where it could be subjected to random and sudden movements, such as a washing machine or a sports bag, is very clear.

DESCRIPTION OF THE INVENTION

The inconveniences cited above are solved with the device of the invention, which also exhibits other advantages that are described below.

The active substance dispensing device of this invention comprises an active substance dispensing element and adjustment means for the dispensing of said active substances, said active substance dispensing element being housed inside a casing formed by a first body and a second body that can be coupled to each other and that can rotate with respect to each other.

In addition, according to a preferred embodiment, said adjustment means for the dispensing of active substances comprise at least one opening provided in said first body and at least one tab provided in said second body, such that the relative position between said first and second bodies determines the degree of closure of said opening of the first body by means of said tab of the second body. These adjustment means make it easy to adjust the dispensing of active substances by simply rotating one body with respect to the other.

Advantageously, said first body comprises a plurality of holes supplementary to a protrusion provided in said second body, the position of said protrusion inside one of said holes determining varying adjustment positions of the degree of closure of said opening, and said protrusion being preferably arranged at the end of an elastic flange of said second body.

Thanks to these characteristics, the connection between said first and second bodies is very strong and there are no longitudinal or axial movements between them once they are coupled. Thus, the dispensing device of the present invention is suitable for use in places where it may be subjected to random and abrupt movements, such as a washing machine or a sports bag, for example.

Preferably, said first and second bodies are made of plastic, and said active substance dispensing element is a tablet coated with active substances or a membrane housing a gel coated with active substances inside.

BRIEF DESCRIPTION OF THE DRAWINGS

With the purpose of facilitating a better comprehension of what has been said above, drawings have been attached, which represent a practical embodiment schematically and in an illustrative rather than limiting matter.

FIGS. 2 to 4 are side views of the device of this invention in three different adjustment positions; in particular, FIG. 2 shows the device in its maximum release position, FIG. 3 in its medium release position, and FIG. 4 in its minimum release position.

DESCRIPTION OF A PREFERRED EMBODIMENT

Figure 1:
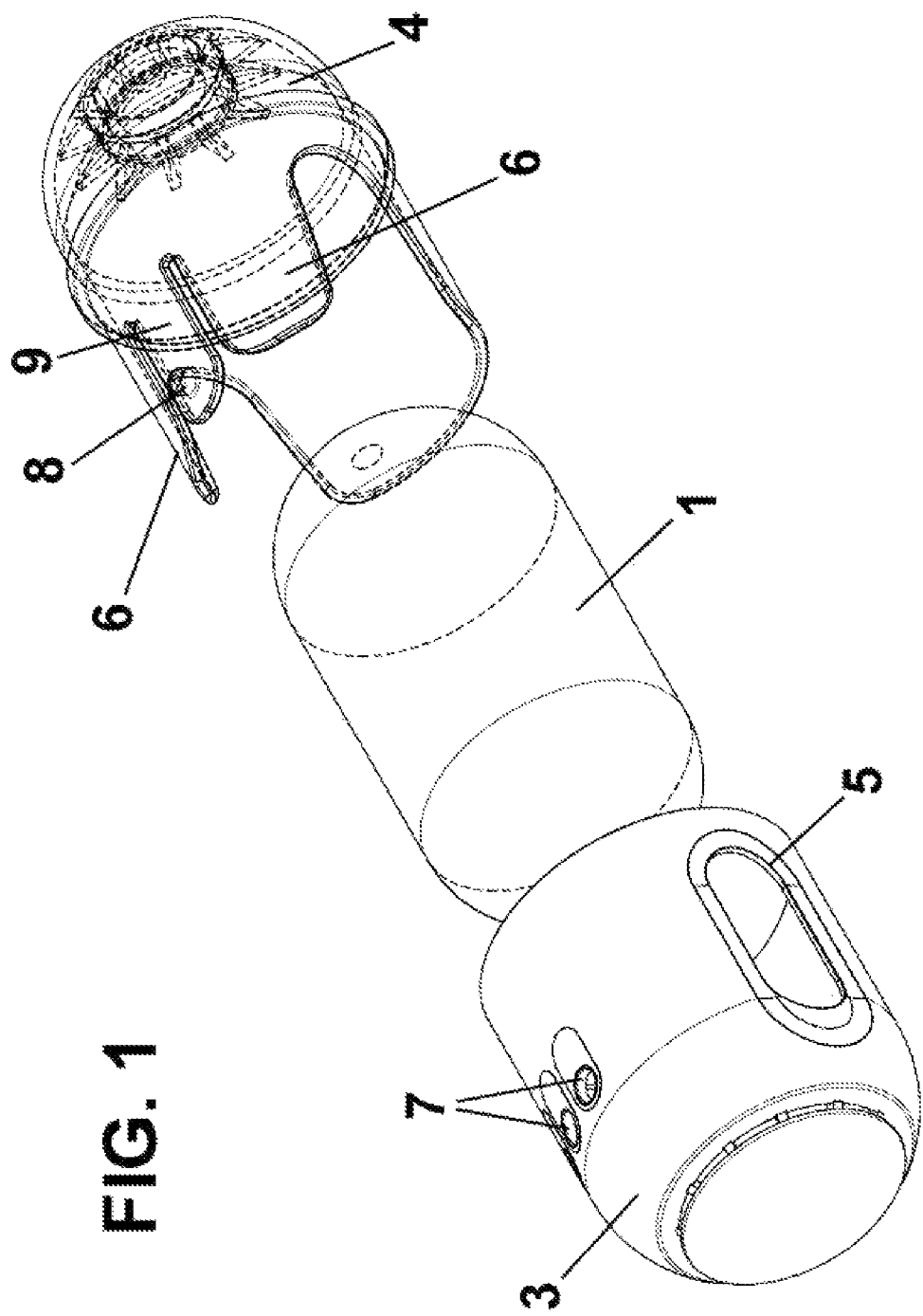
FIG. 1 is an exploded perspective view of the device of this invention.

As shown in FIG. 1, the device of this invention comprises a casing, indicated in general by means of numerical reference 2, fully housing an active substance dispensing element 1 inside, such as soap, bleach, an anti-limescale product, air freshener or insecticide, or a combination thereof.

Said active substance dispensing element 1 may be, for example, a tablet coated with active substances or a membrane housing a gel coated with active substances.

The casing 2 is formed by a first body 3 and a second body 4, preferably made of plastic, that can be coupled to each other and that can rotate with respect to each other. As shown in the figures, each body 3, 4 is provided in the form of a cap with a closed end.

The first body 3 comprises at least one opening 5 to dispense the active substances and a plurality of holes 7 to adjust the relative position between the first body 3 and the second body 4, as shall be explained below.

It should be noted that even though only one opening 5 can be seen in the figures, the first body 3 preferably comprises a second opening arranged symmetrically with respect to the longitudinal axis of said first body 3.

On the other hand, the second body 4 comprises at least one tab 6, two in the case of the represented embodiment. Said or each tab 6 serves to determine the degree of closure of said opening 5, as shown in FIGS. 2 to 4. For an expert in the art it would be clear that the number of tabs 6 and 5 could be greater than 2. An increase in the number of adjustable openings will give the device a greater number of directions, resulting in a device that operates in the same manner in different positions during use.

Furthermore, said second body 4 comprises a protrusion 8 supplementary to said holes 7 of the first body 3. The position of said protrusion 8 in one of said holes 7 determines the degree of closure of said opening(s) 5, as shall be explained below. Said protrusion 8 is preferably placed at the end of an elastic flange 9.

The operation of the device of this invention is the following:

A new dispensing element 1 is placed inside the casing 2, snapping said first 3 and second 4 bodies into place. This is achieved by introducing the protrusion 8 into one of said holes 7.

In order to adjust the release of active substances through the opening(s) 5, the second body 4 needs to rotate with respect to the first body 3. This is achieved by pushing the protrusion 8 through the hole 7 where it is housed, such that it comes out from said hole 7 due to the elastic nature of the flange 9, and by rotating the second body 4 until the protrusion 8 is introduced in another hole 7. This way, it is much more difficult for the adjustment to be modified in an accidental manner due to external friction.

Furthermore, if desired, the device of this invention could provide the decoupling of the first and second bodies 3, 4 from one another to couple them once again in a different position to adjust the release of the active substances. This option could be used for cases where the device is intended for use in situations of extreme stress.

To facilitate the identification of the degree of closure of said opening(s) 5, each hole 7 is associated with a code, for example, a color code, for identification purposes.

FIGS. 2 to 4 show the three possible degrees of closure or release of active substances according to the represented embodiment. In particular, FIG. 2 shows the device in its maximum release position, FIG. 3 in its medium release position, and FIG. 4 in its minimum release position.

Although reference has been made to a specific embodiment of the invention, for an expert in the art it would be clear that the device described herein is susceptible to numerous variations and modifications, and that all the details mentioned herein can be replaced by other, technically equivalent details without diverging from the scope of protection defined by the claims attached hereto.

The invention claimed is:

1. An active substance dispensing device comprising an active substance dispensing element (1) and adjustment means for dispensing said active substances, said active substance dispensing element (1) being housed inside a casing (2) formed by a first body (3) and a second body (4) that can be coupled to each other and that can rotate with respect to each other, characterized in that said adjustment means of the dispensing of active substances comprise at least one opening (5) provided in said first body (3) and at least one tab (6) provided in said second body (4), such that the relative position between said first (3) and second (4) bodies determines the degree of closure of said opening (5) of the first body by means of said tab (6) of the second body (4), and in that said first body (3) comprises a plurality of holes (7) supplementary to a protrusion (8) provided in said second body (4), the position of said protrusion (8) inside one of said holes (7) determining varying adjustment positions of the degree of closure of said opening (5).

2. The active substance dispensing device according to claim 1, wherein said protrusion (8) is arranged at the end of a flange (9) of said second body (4).

3. The active substance dispensing device according to claim 2, wherein said flange (9) is elastic.

4. The active substance dispensing device according to claim 1, wherein said first (3) and second (4) bodies are made of plastic.

5. The active substance dispensing device according to claim 1, wherein said active substance dispensing element (1) is a tablet coated with active substances or a membrane housing a gel coated with active substances inside.

* * * * *